US010881680B2

(12) United States Patent
Olhava et al.

(10) Patent No.: US 10,881,680 B2
(45) Date of Patent: *Jan. 5, 2021

(54) METHOD OF TREATING LEUKEMIA

(71) Applicant: Epizyme, Inc., Cambridge, MA (US)

(72) Inventors: Edward J. Olhava, Newton, MA (US); Richard Chesworth, Concord, MA (US); Kevin W. Kuntz, Woburn, MA (US); Victoria M. Richon, Wellesley, MA (US); Roy M. Pollock, Medford, MA (US); Scott Richard Daigle, Newburyport, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/214,783

(22) Filed: Dec. 10, 2018

(65) Prior Publication Data

US 2019/0216838 A1 Jul. 18, 2019

Related U.S. Application Data

(63) Continuation of application No. 15/387,240, filed on Dec. 21, 2016, now abandoned, which is a continuation of application No. 14/426,331, filed as application No. PCT/US2013/058537 on Sep. 6, 2013, now Pat. No. 9,597,348.

(60) Provisional application No. 61/697,721, filed on Sep. 6, 2012.

(51) Int. Cl.
*A61K 31/7076* (2006.01)
*A61K 31/52* (2006.01)

(52) U.S. Cl.
CPC .......... *A61K 31/7076* (2013.01); *A61K 31/52* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 5,763,263 | A | 6/1998 | Dehlinger |
| 7,576,069 | B2 | 8/2009 | Rieger et al. |
| 8,580,762 | B2 | 11/2013 | Olhava et al. |
| 8,722,877 | B2 | 5/2014 | Chesworth et al. |
| 9,012,166 | B2 | 4/2015 | Nishino et al. |
| 9,029,343 | B2 | 5/2015 | Chesworth et al. |
| 9,096,634 | B2 | 8/2015 | Olhava et al. |
| 9,145,438 | B2 | 9/2015 | Chesworth et al. |
| 9,446,064 | B2 | 9/2016 | Klaus et al. |
| 9,597,348 | B2 * | 3/2017 | Olhava .............. A61K 31/7076 |
| 2004/0147464 | A1 | 7/2004 | Roberts et al. |
| 2006/0040889 | A1 | 2/2006 | Rieger et al. |
| 2006/0189636 | A1 | 8/2006 | Critchley et al. |
| 2006/0235037 | A1 | 10/2006 | Purandare et al. |
| 2007/0191293 | A1 | 8/2007 | Langston et al. |
| 2008/0064653 | A1 | 3/2008 | Li et al. |
| 2008/0132525 | A1 | 6/2008 | Wahhab et al. |
| 2009/0105476 | A1 | 4/2009 | Fairhurst et al. |
| 2010/0144655 | A1 | 6/2010 | Chen et al. |
| 2012/0122895 | A1 | 5/2012 | Jiang et al. |
| 2013/0029878 | A1 | 1/2013 | Nishino et al. |
| 2013/0310334 | A1 | 11/2013 | Chesworth et al. |
| 2013/0338173 | A1 | 12/2013 | Olhava et al. |
| 2014/0051654 | A1 | 2/2014 | Olhava et al. |
| 2014/0100184 | A1 | 4/2014 | Song et al. |
| 2014/0323421 | A1 | 10/2014 | Klaus et al. |
| 2015/0011495 | A1 | 1/2015 | Olhava |
| 2015/0284422 | A1 | 10/2015 | Olhava et al. |
| 2015/0342979 | A1 | 12/2015 | Pollock et al. |
| 2015/0366893 | A1 | 12/2015 | Olhava et al. |
| 2016/0045531 | A1 | 2/2016 | Klaus et al. |
| 2016/0298195 | A1 | 10/2016 | Armstrong |
| 2017/0137455 | A1 | 5/2017 | Olhava et al. |
| 2017/0165288 | A1 | 6/2017 | Olhava et al. |
| 2017/0335402 | A1 | 11/2017 | Rau et al. |
| 2019/0276899 | A1 | 9/2019 | Bernt et al. |
| 2020/0080155 | A1 | 3/2020 | Rau et al. |
| 2020/0113923 | A1 | 4/2020 | Pollock et al. |

FOREIGN PATENT DOCUMENTS

| | | |
|---|---|---|
| CN | 102066372 A | 5/2011 |
| EP | 1 138 688 A1 | 10/2001 |
| EP | 2 208 721 A1 | 7/2010 |
| EP | 2 562 264 A1 | 2/2013 |
| JP | 2008-295444 A | 12/2008 |
| JP | 2010-46057 A | 3/2010 |
| JP | 2011-239775 A | 12/2011 |
| WO | WO 2001/072764 A1 | 10/2001 |
| WO | WO 2001/077075 A2 | 10/2001 |

(Continued)

OTHER PUBLICATIONS

Anglin, J.L. and Y. Song (2013) "A Medicinal Chemistry Perspective for Targeting Histone H3 Lysine-79 Methyltransferase DOT1L", *J Med Chem*, 56:8972-8983.

Basavapathruni, A. et al. (Oct. 9, 2012) "Conformational Adaptation Drives Potent, Selective and Durable Inhibition of the Human Protein Methyltransferase DOT1L" *Chem Biol Drug Des*, 80(6):971-980.

Bernt, K.M. et al. (Nov. 2010) "Demonstration of a Role for Dot1l in MLL-Rearranged Leukemia Using a Conditional Loss of Function Model" Abstract of Oral Session presented at the 53rd ASH Annual Meeting and Exposition, Dec. 10-12, 2011. *Blood*, 116(21):62, 2 pages.

Bernt, K.M. et al. (Jul. 12, 2011) "MLL-rearranged leukemia is dependent on aberrant H3K79 methylation by DOT1L" *Cancer Cell*, 20:66-78.

(Continued)

*Primary Examiner* — Traviss C McIntosh, III
(74) *Attorney, Agent, or Firm* — Cooley LLP; Heidi A. Erlacher; Xixi Sun

(57) ABSTRACT

The present invention relates to methods of treating disorders in which DOT1L-mediated protein methylation plays a part, such as cancer, by administering DOT1L inhibitor compounds and pharmaceutical compositions to subjects in need thereof.

20 Claims, 3 Drawing Sheets

(56) References Cited

FOREIGN PATENT DOCUMENTS

| WO | WO 2002/100152 A2 | 12/2002 |
|---|---|---|
| WO | WO 2003/074083 A1 | 9/2003 |
| WO | WO 2004/007512 A2 | 1/2004 |
| WO | WO 2004/022572 A1 | 3/2004 |
| WO | WO 2006/015357 A2 | 2/2006 |
| WO | WO 2006/025832 A1 | 3/2006 |
| WO | WO 2006/028618 A1 | 3/2006 |
| WO | WO 2006/063058 A2 | 6/2006 |
| WO | WO 2006/078752 A2 | 7/2006 |
| WO | WO 2006/113615 A2 | 10/2006 |
| WO | WO 2007/100304 A1 | 9/2007 |
| WO | WO 2008/041767 A1 | 4/2008 |
| WO | WO 2008/124150 A1 | 10/2008 |
| WO | WO 2009/089425 A1 | 7/2009 |
| WO | WO 2010/027005 A1 | 3/2010 |
| WO | WO 2010/048149 A2 | 4/2010 |
| WO | WO 2011/023081 A1 | 6/2012 |
| WO | WO 2012/075381 A1 | 6/2012 |
| WO | WO 2012/075492 A2 | 6/2012 |
| WO | WO 2012/075500 A2 | 6/2012 |
| WO | WO 2012/082436 A2 | 6/2012 |
| WO | WO 2014/026198 A1 | 2/2014 |
| WO | WO 2014/035140 A2 | 3/2014 |
| WO | WO 2014/100662 A1 | 6/2014 |
| WO | WO 2015/017863 A1 | 2/2015 |

OTHER PUBLICATIONS

Böiers, C. et al. (2013) "Lymphomyeloid contribution of an immune-restricted progenitor emerging prior to definitive hematopoietic stem cells" *Cell Stem Cell*, 13:535-548.

Buijs, A. et al. (1995) "Translocation (12;22) (p13;q11) in myeloproliferative disorders results in fusion of the ETS-like TEL gene on 12p13 to the MN1 gene on 22q11" *Oncogene*, 10:1511-1519.

Carella, C. et al. (2007) "MN1 overexpression is an important step in the development of inv(16) AML" *Leukemia*, 21:1679-1690.

Chen, L. et al. (2012) "Abrogation of MLL-AF10 and CALM-AF10 Mediated Transformation Through Genetic Inactivation or Pharmacological Inhibition of the H3K79 Methyltransferase DOT1L" *Blood*, 120(21):2384.

Chen, L. et al. (Apr. 2013) "Abrogation of MLL-AF10 and CALM-AF10 Mediated Transformation Through Genetic Inactivation or Pharmacological Inhibition of the H3K79 Methyltransferase DOT1L" *Leukemia*, 27(4):813-822. NIH Public Access Author Manuscript, available in PMC Apr. 1, 2014 22 pages.

Chen, Y. et al. (2013) "Prognostic significance of 11q23 aberrations in adult acute myeloid leukemia and the role of alloeneic stem cell transplantation" *Leukemia*, 27:836-842.

Chung, Y.R. et al. (2012) "Epigenetic alterations in hematopoietic malignancies" *International Journal of Hematology*, 96(4):413-427.

Copeland, R.A. (2012) "Protein methyltransferase inhibitors as personalized cancer therapeutics" *Drug Discov Today Ther Strateg*, 9(2-3):e83-e90.

Cozzio, A. et al. (2003) "Similar MLL-associated leukemias arising from self-renewing stem cells and short-lived myeloid progenitors" *Genes & Development*, 17:3029-3035.

Daigle, S.R. et al. (Jul. 2011) "Selective Killing of Mixed Lineage Leukemia Cells by a Potent Small-Molecule DOT1L Inhibitor" *Cancer Cell*, 20(1):53-65.

Daigle, S.R. et al. (Aug. 8, 2013) "Potent inhibition of DOT1L as treatment of MLL-fusion leukemia" *Blood*, 122:1017-1025.

Deshpande, A.J. et al. (Dec. 8, 2014) "AF10 Regulates Progressive H3K79 Methylation and HOX Gene Expression in Diverse AML Subtypes" *Cancer Cell*, 26(6):896-908.

Drexler, H.G. et al. (2009) "Many are called MDS cell lines: One is chosen" *Leukemia Res*, 33:1011-1016.

Essers, M.A. et al. (Apr. 16, 2009) "IFNalpha activates dormant haematopoietic stem cells in vivo" *Nature*, 458:904-908.

Factor, D.C. et al. (Jun. 5, 2014) "Epigenomic Comparison Reveals Activation of "Seed" Enhancers during Transition from Naive to Primed Pluripotency" *Cell Stem Cell*, 14:854-863.

Gao, W-L. and H-L. Liu (2007) "DOT1: A distinct class of histone lysine methyltransferase" *Hereditas*, 29(12):1449-1454. Chinese with English abstract on p. 1449.

Grosveld, G.C. (2007) "MN1, a novel player in human AML" *Blood Cells, Molecules & Diseases*, 39:336-339.

Guo, G. et al. (Oct. 3, 2013) "Mapping cellular hierarchy by single-cell analysis of the cell surface repertoire" *Cell Stem Cell* 13:492-505.

Haferlach, C. et al. (2012) "Gene expression of BAALC, CDKN1B, ERG, and MN1 adds independent prognostic information to cytogenetics and molecular mutations in adult acute myeloid leukemia" *Genes, Chromosomes & Cancer*, 51:257-265.

Hattori, N. et al. (2014) "Compendium of aberrant DNA methylation and histone modifications in cancer" *Biochemical and Biophysical Research Communications*, 455(1-2):3-9.

Heuser, M. et al. (Dec. 1, 2006) "High meningioma 1 (MN1) expression as a predictor for poor outcome in acute myeloid leukemia with normal cytogenetics" *Blood*, 108(12):3898-3905.

Heuser, M. et al. (Sep. 1, 2007) "MN1 overexpression induces acute myeloid leukemia in mice and predicts ATRA resistance in patients with AML" *Blood*, 110:1639-1647.

Heuser, M. et al. (Jul. 12, 2011) "Cell of origin in AML: susceptibility to MN1-induced transformation is regulated by the MEIS1/AbdB-like HOX protein complex" *Cancer Cell*, 20:39-52.

Ilencikova, D. et al. (2013) "MLL Gene Alterations in Acute Myeloid Leukaemia (11q23//MLL+ AML)" Chapter 10 in *Oncogene and Cancer—From Bench to Clinic*, pp. 225-246. InTechOpen [online]. Retrieved from: www.intechopen.com/books/oncogene-and-cancer-from-bench-to-clinic.

Im, A.P. et al. (2014) "DNMT3A and IDH mutations in acute myeloid leukemia and other myeloid malignancies: associations with prognosis and potential treatment strategies" *Leukemia*, 28(9):1774-1783.

Jacinto, F.V. et al. (2009) "Impaired recruitment of the histone methyltransferase DOT1L contributes to the incomplete reactivation of tumor suppressor genes upon DNA demethylation" *Oncogene*, 28:4212-4224.

Jiang, X. et al. (Oct. 2012) "Blockade of miR-150 Maturation by MLL-Fusion/MYC/Lin-28 Is Required for MLL-Associated Leukemia" *Blood*, 120(21:3499 [online]. Retrieved from: http://www.bloodjournal.org/content/120/21/3499, 7 pages.

Jiang, X. et al. (Oct. 2012) "Blockade of miR-150 Maturation by MLL-Fusion/MYC/Lin-28 Is Required for MLL-Associated Leukemia" *Cancer Cell*, 22(4):524-535.

Jo, S.Y. et al. (May 5, 2011) "Requirement for Dot11 in murine postnatal hematopoiesis and leukemogenesis by MLL translocation" *Blood*, 117:4759-4768.

Klaus, C.R. et al. (Sep. 2014) "DOT1L Inhibitor EPZ-5676 Displays Synergistic Antiproliferative Activity in Combination with Standard of Care Drugs and Hypomethylating Agents in MLL-Rearranged Leukemia Cells" *J Pharmacol Exp Ther*, 350:646-656.

Klco, J.M. et al. (Feb. 28, 2013) "Genomic impact of transient low-dose decitabine treatment on primary AML cells" *Blood*, 121:1633-1643.

Krivtsov, A.V. et al. (Aug. 17, 2006) "Transformation from committed progenitor to leukaemia stem cell initiated by MLL-AF9" *Nature*, 442:818-822.

Krivtsov, A.V. et al. (2013) "Cell of origin determines clinically relevant subtypes of MLL-rearranged AML" *Leukemia*, 27:852-860.

Langer, C. et al. (2009) "Prognostic importance of MN1 transcript levels, and biologic insights from MN1-associated gene and microRNA expression signatures in cytogenetically normal acute myeloid leukemia: a cancer and leukemia group B study" *Journal of Clinical Oncology*, 27:3198-3204.

Lekanne Deprez, R.H. et al. (1995) "Cloning and characterization of Mn1, a gene from chromosome 22q11, which is disrupted by a balanced translocation in a meningioma" *Oncogene*, 10:1521-1528.

(56) References Cited

OTHER PUBLICATIONS

Li, Y. et al. (Mar. 4, 2003) "Selective killing of cancer cells by β-lapachone: Direct checkpoint activation as a strategy against cancer" *PNAS*, 100(5):2674-2678.

Liu, T. et al. (2010) "Functional characterization of high levels of meningioma 1 as collaborating oncogene in acute leukemia" *Leukemia*, 24(3):601-612.

Liu, W. et al. (May 2014) "DOT1L Inhibition Sensitizes MLL-Rearranged AML to Chemotherapy" *PLoS One*, 9(5):e98270, 11 pages.

Marrone, T.J. et al. (1997) "Structure-based Drug Design: Computational Advances" *Annu Rev Pharmacol Toxicol*, 37:71-90.

Metzeler, K.H. et al. (Oct. 20, 2009) "ERG Expression Is an Independent Prognostic Factor and Allows Refined Risk Stratification in Cytogenetically Normal Acute Myeloid Leukemia: A Comprehensive Analysis of ERG, MN1, and BAALC Transcript Levels Using Oligonucleotide Microarrays" *Journal of Clinical Oncology*, 27:5031-5038.

Metzler, K.H. et al. (2012) "DNMT3A mutations and response to the hypomethylating agent decitabine in acute myeloid leukemia" Letters to the Editor; *Leukemia*, 26(5):1106-1107.

Min, J. et al. (Mar. 7, 2013) "Structure of the Catalytic Domain of Human DOT1L, a Non-SET Domain Nucleosomal Histone Methyltransferase" *Cell*, 112(5):711-723.

Nguyen, A.T. et al. (2011) "Essential role of DOT1L in maintaining normal adult hematopoiesis" *Cell Research*, 21:1370-1373.

Olver, I. (2000) "Chemotherapy for elderly patients with advanced cancer: is it worth it?", Australian Prescriber, vol. 23, pp. 80-82 [online]. Retrieved from: https://www.nps.org.au/australian-prescriber/articles/chemotherapy-for-elderly-patients-with-advanced-cancer-is-it-worth-it, 4 pages.

Pollock, R.M. et al. (2010) "Selective Killing of Mixed Lineage Leukemia Cells by a Potent Small-Molecule DOT1L Inhibitor" *Blood*, 116(21):342, Abstract 780 [online]. Retrieved from: http://www.bloodjournal.org/content/116/21/780; retrieved on Dec. 19, 2017, 5 pages.

Rau, R.E. et al. (2014) "DOT1L as a Therapeutic Target for the Treatment of DNMT3A-Mutant Acute Myeloid Leukemia" *Blood*, 124(21):614; abstract, 1 page.

Rau, R.E. et al. (Aug. 18, 2016) "DOT1L as a therapeutic target for the treatment of DNMT3A-mutant acute myeloid leukemia" *Blood*, 128(7):971-981.

Russler-Germain et al. (Apr. 14, 2014) "The R882H DNMT3A Mutation Associated with AML Dominantly Inhibits Wild-Type DNMT3A by Blocking Its Ability to Form Active Tetramers" *Cancer Cell*, 25(4):442-454.

Sarkaria, S.M. et al. (2014) "Primary acute myeloid leukemia cells with IDH1 or IDH2 mutations respond to a DOT1L inhibitor in vitro" *Leukemia*, 28:2403-2406.

Seifert, M. et al. (Jan. 1, 2008) "Essential Factors for Successful Virtual Screening" *Mini Reviews in Medicinal Chemistry*, 8(1):63-72.

Stein, E.M. et al. (May 3, 2018) "The DOT1L inhibitor pinometostat reduces H3K79 methylation and has modest clinical activity in adult acute leukemia" *Blood*, [prepublished online]. Retrieved on Jun. 11, 2018 from: www.bloodjournal.org, doi:10.1182/blood-2017-12-818948, 30 pages.

Van Wely, K.H.M. et al. (2007) "The MN1-TEL myeloid leukemia-associated fusion protein has a dominant-negative effect on RAR-RXR-mediated transcription" *Oncogene*, 26:5733-5740.

Waters, N.J. et al. (Dec. 2015) "Exploring drug delivery for the DOT1L inhibitor pinometostat (EPZ-5676): Subcutaneous administration as an alternative to continuous IV infusion, in the pursuit of an epigenetic target" *Journal of Controlled Release, Part B*, 220:758-765.

Wouters, B.J. et al. (Jan. 8, 2009) "A decade of genome-wide gene expression profiling in acute myeloid leukemia: flashback and prospects" *Blood*, 113(2):291-298.

Wouters, B.J. et al. (Mar. 26, 2009) "Double CEBPA mutations, but not single CEBPA mutations, define a subgroup of acute myeloid leukemia with a distinctive gene expression profile that is uniquely associated with a favorable outcome" *Blood*, 113(13):3088-3091.

Xiang, L.et al. (2013) "The clinical characteristics and prognostic significance of MN1 gene and MN1-associated microRNA expression in adult patients with de novo acute myeloid leukemia" *Annals of Hematology*, 92:1063-1069.

Yang. L. et al. (Mar. 2015) "DNMT3A in haematological malignancies" *Nature Reviews: Cancer*, 15(3):152-165.

Yao, Y. et al. (Oct. 26, 2011) "Selective Inhibitors of Histone Methyltransferase DOT1L: Design, Synthesis, and Crystallographic Studies" *J Am Chem Soc*, 133(42):16746-16749.

Yu, W. et al. (Dec. 18, 2012) "Catalytic site remodelling of the DOT1L methyltransferase by selective inhibitors" *Nature Commun*, 3:1288; DOI: 10.1038/ncomms2304, 12 pages.

\* cited by examiner

METHOD OF TREATING LEUKEMIA

RELATED APPLICATIONS

This application is a continuation of U.S. application Ser. No. 15/387,240, filed on Dec. 21, 2016, which is a continuation application of U.S. application Ser. No. 14/426,331, filed on Mar. 5, 2015 (now U.S. Pat. No. 9,597,348), which is a U.S. National Phase application of International Application No. PCT/US2013/058537, filed on Sep. 6, 2013, which claims priority to, and the benefit of, U.S. Provisional Application No. 61/697,721, filed Sep. 6, 2012, the entire contents of each of which are incorporated herein in their entireties.

BACKGROUND OF THE INVENTION

Disease-associated chromatin-modifying enzymes (e.g., DOT1L) play a role in diseases such as proliferative disorders, metabolic disorders, and blood disorders. Thus, there is a need for the development of small molecules that are capable of modulating the activity of DOT1L.

SUMMARY OF THE INVENTION

The present invention provides a method for treating cancer by administering to a subject in need thereof a therapeutically effective amount of a compound of Formula (I) (i.e., Compound 2) or its N-oxide or a pharmaceutically acceptable salt thereof:

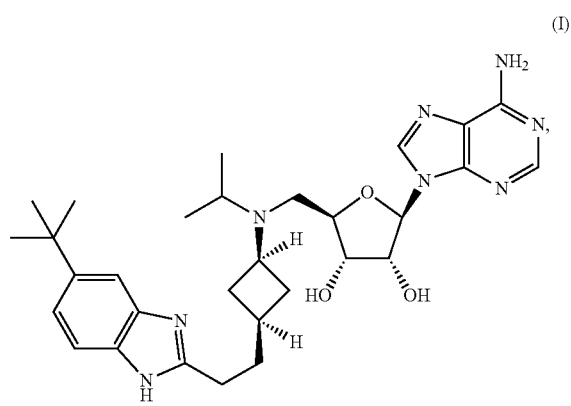 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

(I)

where the subject had at least one prior therapy to treat a hematological cancer.

For example, the hematological cancer is refractory to the prior therapy. For example, the hematological cancer shows recurrence following remission. In some embodiments, the subject received and failed all known effective therapies for the hematological cancer.

In some embodiments, the subject has a hematological cancer selected from the group consisting of acute myeloid leukemia, acute lymphoblastic leukemia, myelodysplastic syndrome, a myeloproliferative disorder, and chronic myelogenous leukemia.

In some embodiments, the subject treated by the methods of the invention has leukemia. For example, the leukemia is characterized by MLL gene rearrangement. In some embodiments, the MLL gene rearrangement is translocation of the MLL gene at 11q23. In some embodiments, the MLL gene rearrangement is a partial tandem duplication of the MLL gene.

The present invention also provides a method for treating cancer by administering to a subject in need thereof a therapeutically effective amount of a compound of Formula (I) (i.e., Compound 2) or its N-oxide or a pharmaceutically acceptable salt thereof:

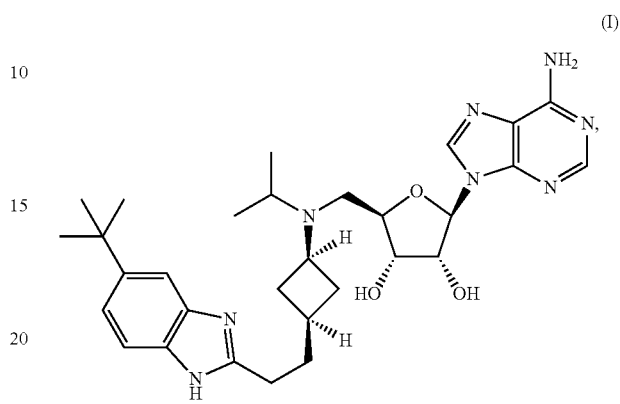

(I)

where the subject is unable to receive other therapy to treat the cancer due to age or intercurrent illness.

In any methods described herein, the subject may be simultaneously treated with another therapy to treat acute myeloid leukemia, acute lymphoblastic leukemia, myelodysplastic syndrome, a myeloproliferative disorder, or chronic myelogenous leukemia. For example, the another therapy is standard of care for the treatment of acute myeloid leukemia. For example, the another therapy is standard of care for the treatment of acute lymphoblastic leukemia.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figures 1A, 1B:
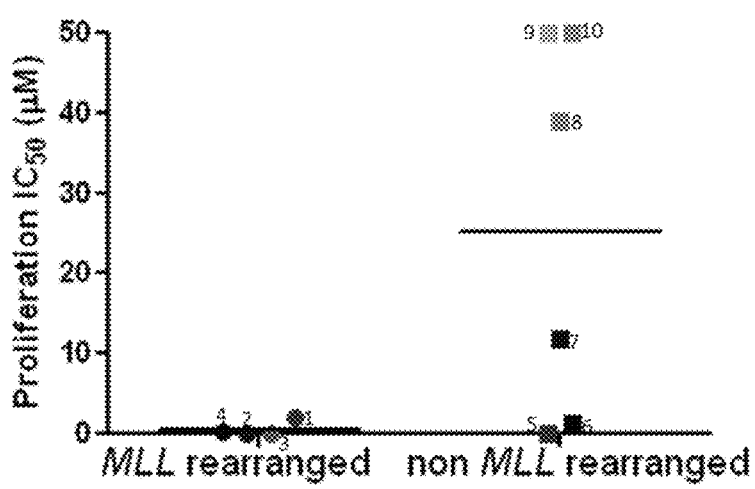
FIGS. 1A and 1B are respectively a table and a plot demonstrating the potency and selectivity of the anti-proliferative activity of Compound 2 using a panel of MLL-rearranged and non-MLL-rearranged human leukemia cell lines. The cell lines used in the study are listed in FIG. 1A.

The present invention provides methods and uses of a compound having the following formula (I) (Compound 2) or its N-oxide or a pharmaceutically acceptable salt thereof for treating cancer, particularly for treating leukemia:

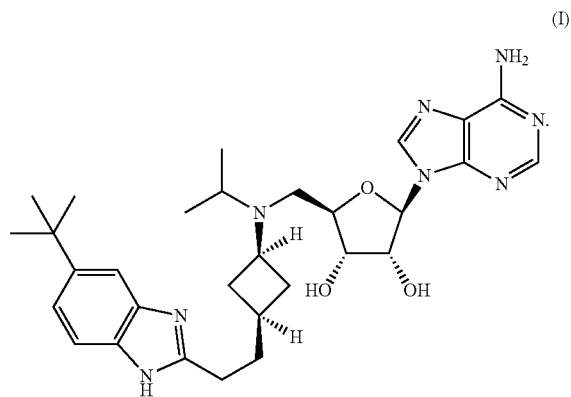 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

(I)

The present invention provides methods for the treatment of leukemia in a subject in need thereof by administering to a subject in need of such treatment, a therapeutically effective amount of a compound of the present invention, or a pharmaceutically acceptable salt, prodrug, metabolite, polymorph or solvate thereof. The leukemia can be acute or chronic leukemia. Preferably, the leukemia is acute myeloid leukemia, acute lymphocytic leukemia or mixed lineage leukemia. The present invention further provides the use of a compound of the present invention, or a pharmaceutically acceptable salt, prodrug, metabolite, polymorph or solvate thereof, for the preparation of a medicament useful for the treatment of leukemia. The leukemia can be acute or chronic leukemia. For example, the leukemia can be acute myeloid leukemia, acute lymphocytic leukemia or mixed lineage leukemia, myelodysplastic syndrome, a myeloproliferative disorder, or chronic myelogenous leukemia. Exemplary myeloproliferative disorder includes, for example, but is not limited to, chronic myelogenous leukemia (CML), polycythemia vera (PV), essential thrombocytosis (ET), or myelofibrosis (MF).

The present invention provides methods for the treatment of a disease or disorder mediated by rearrangements of the MLL gene in a subject in need thereof by administering to the subject in need of such treatment, a therapeutically effective amount of a compound of the present invention, or a pharmaceutically acceptable salt, prodrug, metabolite, polymorph or solvate thereof. In certain embodiments the MLL rearrangement is a translocation of a gene on chromosome 11q23. In certain embodiments the MLL rearrangement is partial tandem duplication (MLL-PTD). The present invention further provides the use of a compound of the present invention, or a pharmaceutically acceptable salt, prodrug, metabolite, polymorph or solvate thereof, for the preparation of a medicament useful for the treatment of a disease or disorder mediated by MLL gene rearrangements.

As used herein, a "subject in need thereof" is a subject having cancer, or hematologic cancer or leukemia. For example, the leukemia is acute myeloid leukemia, acute lymphoblastic leukemia, acute mixed lineage leukemia, myelodysplastic syndrome, a myeloproliferative disorder, or chronic myelogenous leukemia. For example, the subject has a leukemia involving translocation of the MLL gene at 11q23, MLL-PTD or an advanced hematologic malignancy. In certain embodiments the subject is the subject is unable to receive other therapy to treat the cancer due to age or intercurring illness. In certain embodiments the subject is at least 50 years old, or at least 60 years old, or at least 65 years old, or at least 70 years old or older.

In some embodiments, the subject in need thereof had at least one prior therapy to treat acute myeloid leukemia, acute lymphoblastic leukemia, acute mixed lineage leukemia, myelodysplastic syndrome, a myeloproliferative disorder, or chronic myelogenous leukemia.

In some embodiments, the subject has refractory cancer. Refractory cancer is a malignancy for which surgery is ineffective, which is either initially unresponsive to chemo- or radiation therapy, or which becomes unresponsive over time.

In some embodiments, the subject has hematological cancer recurrence following remission.

In some embodiments, the subject is not a candidate for allogeneic stem cell transplantation.

In some embodiments, the subject is simultaneously being treated with another therapy to treat acute myeloid leukemia, acute lymphoblastic leukemia, acute mixed lineage leukemia, myelodysplastic syndrome, a myeloproliferative disorder, or chronic myelogenous leukemia. Additional therapies and agents that can be used to treat these cancers are known to the skilled artisan; and are described in U.S. Provisional Application No. 61/785,446, the contents of which are incorporated herein by reference in their entireties. In certain embodiments the patient is treated with the standard of care treatment as described in the most current National Comprehensive Cancer Network (NCCN) guidelines. For example, for the treatment of AML such therapy may include all-trans retinoic acid (ATRA), cytaribine (Ara-C), daunorubicin, idarubicine, arsenic trioxide (ATO, 6-mercaptopurine and/or methotrexate. For example, for the treatment of ALL the standard of care may include vincristine, corticosteroids such as prednisone, and/or methotrexate.

In some embodiments, the subject received and failed all known effective therapies for the hematological cancer that the subject has or is suffering from.

A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, "monotherapy" refers to the administration of a single active or therapeutic compound to a subject in need thereof. Preferably, monotherapy will involve administration of a therapeutically effective amount of an single active compound. For example, cancer monotherapy with one of the compound of the present invention, or a pharmaceutically acceptable salt, prodrug, metabolite, analog or derivative thereof, to a subject in need of treatment of cancer. In one aspect, the single active compound is a compound of the present invention, or a pharmaceutically acceptable salt, prodrug, metabolite, polymorph or solvate thereof.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is abnormal in the body. Symptoms are felt or noticed by the individual experiencing the symptom, but may not easily be noticed by others. Others are defined as non-health-care professionals.

As used herein the term "sign" is also defined as an indication that something is abnormal in the body. But signs are defined as things that can be seen by a doctor, nurse, or other health care professional.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing cancer can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a protein methyltransferase of interest.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter. Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

An effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention.

The present invention also provides pharmaceutical compositions comprising a compound of the present invention, for example compound having Formula (I) (Compound 2), in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy,* $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds described herein are assayed for modulation of activity, for example, histone methylation, modulation of cell growth and/or $IC_{50}$, described in the examples below.

| Compound | DOT1L $IC_{50}$ (μM) |
|---|---|
| 2 | 0.00074 |

Additional compounds suitable for the methods of the invention, as well as pharmaceutical compositions and uses thereof, are described in WO2012/075381, WO2012/075492, WO2012/082436, and WO2012/75500, the contents of each of which are hereby incorporated by reference in their entireties.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Nuclear magnetic resonance (NMR) spectra were obtained on a Bruker Avance 400 operating at a field strength of 400.130 MHz or a Bruker DRX 500 MHz NMR or HNMR spectra were obtained on a 500 MHz Bruker AVANCE III spectrometer. Common reaction solvents were either high performance liquid chromatography (HPLC) grade or American Chemical Society (ACS) grade, and anhydrous as obtained from the manufacturer unless otherwise noted. LCMS was performed on a Waters Micromass ZMD with a Waters 2795 Separations Module and Waters 996 photodiode array detector and a Waters Micromass ZQ with a Waters 2695 Separations Module and Waters 996 photodiode array detector or a Waters Micromass Platform LCZ single quadrupole mass spectrometer with a Waters 600 solvent delivery module, Waters 515 ancillary pumps, Waters 2487 UV detector and a Gilson 215 autosampler and fraction collector. Or, LCMS analysis was performed using SQ mass spectrometer coupled to AGILENT 1200 Series HPLC. LCMS data, where available, are provided in the examples below as well as in Table 1. The MS data are provided using the convention for m/z in the format, $[M+H]^+$.

The compounds of the present invention can be prepared using known chemical transformations adapted to the particular situation at hand. Additional information can be found in WO2012/075381, WO2012/075492, WO2012/082436, and WO2012/75500, the contents of each of which are hereby incorporated by reference in their entireties.

Example 1

Synthesis of (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol (Compound 2)

Step 1: Synthesis of cis and trans methyl 3-((((3aR,4R,6R,6aR)-6-(6-amino-9H-purin-9-yl)-2,2-dimethyltetrahydrofuro[3,4-d][1,3]dioxol-4-yl)methyl)amino)cyclobutanecarboxylate

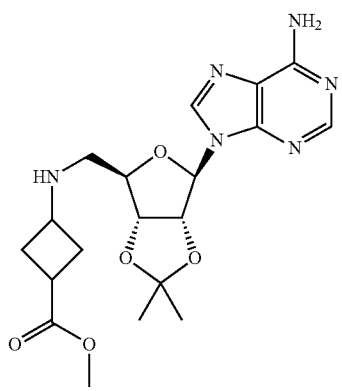 [SMILES: COC(=O)C1CC(NC[C@H]2O[C@@H](n3cnc4c(N)ncnc43)[C@@H]3OC(C)(C)O[C@@H]32)C1]

A solution of methyl 3-oxocyclobutanecarboxylate (4.60 g, 35.94 mmol), 9-((3aR,4R,6R,6aR)-6-(aminomethyl)-2,2-dimethyltetrahydrofuro[3,4-d][1,3]dioxol-4-yl)-9H-purin-6-amine (11.0 g, 35.94 mmol) and Ti(iPrO)$_4$ (4.0 g, 14.08 mmol) in MeOH (80 mL) was stirred at 45° C. for 2 h, then NaCNBH$_3$ (4.5 g, 71.87 mmol) was added. The reaction was stirred at RT overnight. The reaction was quenched with aq. sat. NaHCO$_3$ (40 mL) and filtered, extracted with DCM (80 mL×3), dried over Na$_2$SO$_4$ and concentrated. The residue was purified by preparative-HPLC to obtain the title compound (6.2 g, Yield 41%). $^1$H NMR (500 MHz, CDCl$_3$): δ$_H$ 8.38-8.34 (m, 1H), 7.90 (s, 1H), 5.98 (d, J=3.0 Hz, 1H), 5.75 (br s, 2H), 5.48-5.46 (m, 1H), 5.03-5.01 (m, 1H), 4.35-4.33 (m, 1H), 3.69-3.66 (m, 3H), 3.50-3.17 (m, 1H), 3.05-2.73 (m, 3H), 2.48-2.44 (m, 2H), 1.95-1.91 (m, 2H), 1.62 (s, 3H), 1.39 (s, 3H) ppm; ESI-MS (m/z): 419.2[M+1]$^+$.

The cis/trans mixture of methyl 3-((((3aR,4R,6R,6aR)-6-(6-amino-9H-purin-9-yl)-2,2-dimethyltetrahydrofuro[3,4-d][1,3]dioxol-4-yl)methyl)amino)cyclobutanecarboxylate (6.2 g) was separated via chiral HPLC (CHIRALCEL AD-H 20*250 mm, Sum (Daicel), Column temperature: 35° C., Mobile phase: CO2/Methanol (0.1% DEA)=70/30, Flow rate: 50 g/min) to give the pure cis product (3.5 g) and pure trans product (1.7 g).

Step 2: Synthesis of (1S,3s)-methyl 3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarboxylate

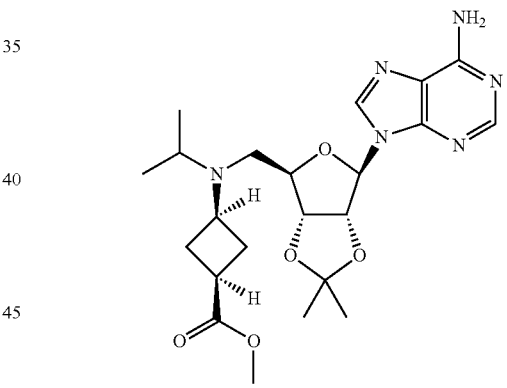

To a solution of cis methyl 3-(((((3aR,4R,6R,6aR)-6-(6-amino-9H-purin-9-yl)-2,2-dimethyltetrahydrofuro[3,4-d][1,3]dioxol-4-yl)methyl)amino)cyclobutanecarboxylate (2.0 g, 4.78 mmol) in CH$_3$CN (15 ml) was added 2-iodopropane (4.0 g, 23.92 mmol) and K$_2$CO$_3$ (1.0 g, 7.18 mmol). The reaction was heated to 95° C. overnight in a sealed tube. The mixture was filtered, the filtrate was concentrated and purified by SGC (DCM:MeOH=12:1) to obtain the title compound (1.9 g, Yield 86%). $^1$H NMR (500 MHz, CDCl$_3$): δ$_H$ 8.37 (s, 1H), 7.89 (s, 1H), 6.03 (d, J=1.5 Hz, 1H), 5.53-5.48 (m, 3H), 5.00 (br s, 1H), 4.25 (brs, 1H), 3.66 (s, 3H), 3.19-3.18 (m, 1H), 2.96 (brs, 1H), 2.80-2.78(m, 1H), 2.67-2.58 (m, 2H), 2.20-2.12 (m, 4H), 1.62 (s, 3H), 1.39 (s, 3H), 1.00 (d, J=6.0 Hz, 3H), 0.84 (d, J=6.0 Hz, 3H) ppm; ESI-MS (m/z): 461.4[M+1]$^+$.

Step 3: Synthesis of (1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarbaldehyde

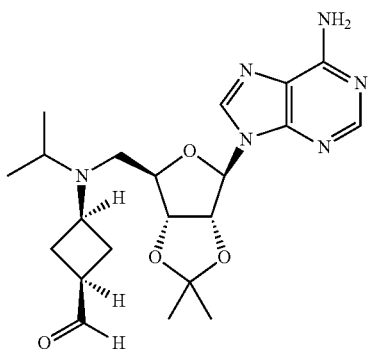 [SMILES: CC(C)N(C[C@H]1O[C@@H](n2cnc3c(N)ncnc32)[C@@H]2OC(C)(C)O[C@@H]21)[C@H]1C[C@@H](C=O)C1]

To a solution of (1S,3s)-methyl 3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarboxylate (1.2 g, 2.60 mmol) in DCM (50 ml) was added DIBAL-H dropwise at −78° C. until all the starting material was consumed as determined by TLC. MeOH (2 ml) was added and the mixture was stirred to RT for 30 min. upon which water (50 ml) was added and the mixture was extracted with DCM (50 ml×2). The organic layer was dried over $Na_2SO_4$ and concentrated to obtain crude title compound (1.0 g which was used) directly in the next step. $^1$H NMR (500 MHz, $CDCl_3$): $\delta_H$ 9.56 (d, J=2.5 Hz, 1H), 8.36 (s, 1H), 7.88 (s, 1H), 6.03 (d, J=2.5 Hz, 1H), 5.66 (br s, 2H), 5.50 (dd, J=2.0, 6.5 Hz, 1H), 5.01 (dd, J=3.5, 6.5 Hz, 1H), 3.331-3.337 (m, 1H), 2.96-2.97 (m, 1H), 2.77-2.59 (m, 3H), 2.14-2.05 (m, 4H), 1.60 (s, 3H), 1.39 (s, 3H), 1.01 (d, J=6.5Hz, 3H), 0.85 (d, J=6.0 Hz, 3H) ppm.

Step 4: Synthesis of (E)-ethyl 3-((1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)acrylate

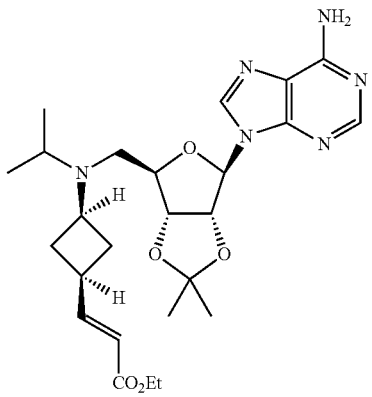 [SMILES: CCOC(=O)/C=C/[C@H]1C[C@@H](N(C[C@H]2O[C@@H](n3cnc4c(N)ncnc43)[C@@H]3OC(C)(C)O[C@@H]32)C(C)C)C1]

To a solution of (1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutane carbaldehyde (930 mg, 2.16 mmol) in $CH_3CN:DCM=5:1$ (50 ml) was added ethyl 2-(diethoxyphosphoryl)acetate (484 mg, 2.16 mmol), DBU (328 mg, 2.16 mmol) and LiCl (91 mg, 2.16 mmol). The mixture was stirred at RT for 1 h and then concentrated. Water (20 ml) was added and the mixture extracted with DCM (25 ml×3). The combined organic layers were dried over $Na_2SO_4$, concentrated and the residue was purified by SGC (DCM:MeOH=30:1) to obtain title compound (900 mg, Yield 83%). $^1$H NMR (500 MHz, $CDCl_3$): $\delta_H$ 8.36 (s, 1H), 7.89 (s, 1H), 6.94-6.90 (m, 1H), 6.03 (s, 1H), 5.72-5.89 (m, 1H), 5.57 (s, 2H), 5.52 (d, J=4.5 Hz, 1H), 5.00 (dd, J=3.5, 6.0 Hz, 1H), 4.25 (d, J=3.0 Hz, 1H), 4.21-4.17 (m, 2H), 3.14 (brs, 1H), 2.961-2.936 (m, 1H), 2.74-2.52 (m, 3H), 2.22-2.14 (m, 2H), 1.79-1.76 (m, 2H), 1.60 (s, 3H), 1.40 (s, 3H), 1.30-1.27 (m, 3H), 1.00 (d, J=7.0 Hz, 3H), 0.82 (d, J=6.5 Hz, 3H) ppm; ESI-MS (m/z): 501.4[M+1]$^+$.

Step 5: Synthesis of ethyl 3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoate

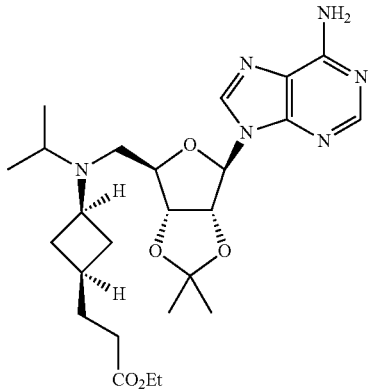 [SMILES: CC(C)N(C[C@H]1O[C@@H](n2cnc3c(N)ncnc32)[C@@H]2OC(C)(C)O[C@@H]21)[C@H]1C[C@@H](CCC(=O)O)C1]

To a solution of (E)-ethyl 3-((1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl) acrylate (900 mg, 1.8 mmol) in MeOH (50 ml) was added Pd/C (20 mg). The mixture was stirred at RT overnight under an atmosphere of hydrogen. The mixture was filtered and the filtrate was concentrated to obtain title compound (700 mg, Yield 78%). $^1$H NMR (500 MHz, $CDCl_3$): $\delta_H$ 8.36 (s, 1H), 7.89 (s, 1H), 6.03 (d, J=2.5 Hz, 1H), 5.69 (s, 2H), 5.51 (dd, J=2.5, 8.0 Hz, 1H), 4.99 (dd, J=4.0, 7.5 Hz, 1H), 4.26 (brs, 1H), 4.13-4.08 (m, 2H), 2.99-2.92 (m, 2H), 2.706-2.655 (m, 1H), 2.539-2.486 (m, 1H), 2.18-2.02 (m, 4H), 1.76 (brs, 1H), 1.65-1.60 (m, 5H), 1.43-1.37 (m, 5H), 1.26-1.23 (m, 2H), 0.97 (d, J=9.0 Hz, 3H), 0.79 (d, J=8.5 Hz, 3H) ppm; ESI-MS (m/z): 503.4[M+1]$^+$.

Step 6: Synthesis of 3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoic acid

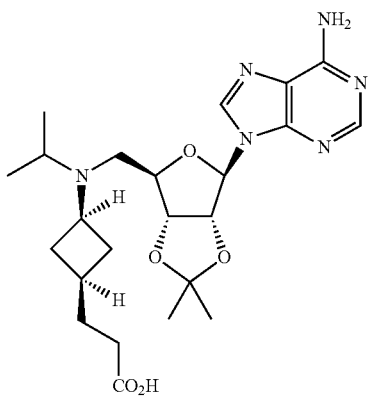

To a solution of ethyl 3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl) (isopropyl)amino)cyclobutyl) propanoate (650 mg, 1.29 mmol) in THF:MeOH=5:1 (30 ml) was added LiOH.H₂O (543 mg, 1.29 mmol). The mixture was stirred at RT overnight, concentrated and then taken up in MeOH (10 ml). 1M HCl solution was added dropwise at 0° C. until pH=7. The mixture was concentrated and purified with preparative-HPLC to give title compound (170 mg).

Step 7: Synthesis of N-(2-amino-4-(tert-butyl)phenyl)-3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl) propanamide

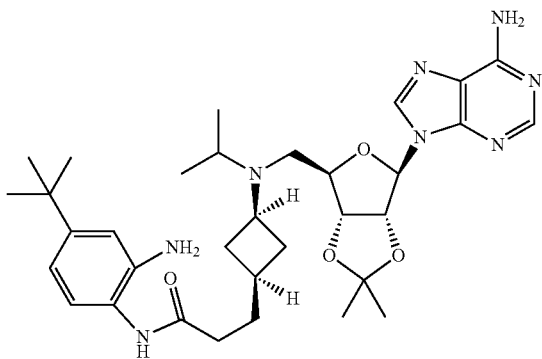 [SMILES: CC(C)N(C[C@H]1O[C@@H](n2cnc3c(N)ncnc32)[C@@H]2OC(C)(C)O[C@@H]21)[C@H]1C[C@@H](CCC(=O)Nc2ccc(C(C)(C)C)cc2N)C1]

To a solution of 3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoic acid (170 mg, 0.36 mmol) in DCM (15 ml) was added 4-tert-butylbenzene-1,2-diamine (117 mg, 0.72 mmol), EDCI (137 mg, 0.72 mmol), HOBT (97 mg, 0.72 mmol) and TEA (217 mg, 2.15 mmol). The mixture was stirred at RT overnight and concentrated. Saturated NaHCO₃ solution (20 ml) was added and the mixture extracted with DCM (20 ml×3). The organic layers were dried over Na₂SO₄ and concentrated. The crude was purified with preparative-TLC (DCM:MeOH=12:1) to afford the title compound (110 mg crude).

Step 8: Synthesis of 9-((3aR,4R,6R,6aR)-6-((((1r,3S)-3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine

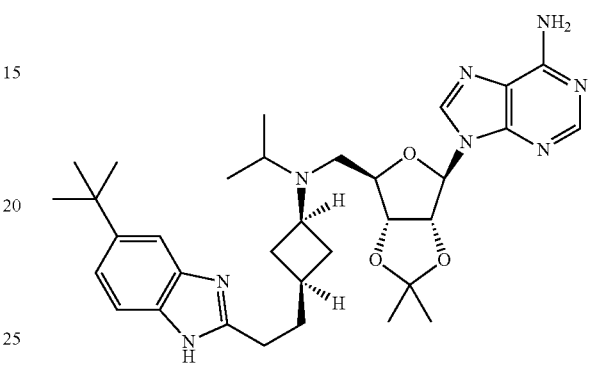

A solution of N-(2-amino-4-(tert-butyl)phenyl)-3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanamide (110 mg) in AcOH (10 ml) was heated to 65° C. overnight. The mixture was concentrated, saturated NaHCO₃ solution (20 ml) was added and the mixture extracted with DCM (20 ml×3). The combined organic layers were dried over Na₂SO₄ and concentrated to give the title compound (105 mg crude). $^1$H NMR (500 MHz, CDCl₃): $\delta_H$ 8.36 (s, 1H), 7.89 (s, 1H), 7.48-7.24 (m, 3H), 6.01 (d, J=1.5 Hz, 1H), 5.60-5.53 (m, 3H), 4.98 (dd, J=3.0, 6.5 Hz, 1H), 4.22 (brs, 1H), 2.97 (brs, 1H), 2.874-2.847 (m, 1H), 2.56-2.50 (m, 3H), 1.87-1.78 (m, 2H), 1.70-1.54 (m, 7H), 1.35-1.17 (m, 14H), 0.90 (d, J=6.5 Hz, 3H), 0.80 (d, J=6.5 Hz, 3H) ppm; ESI-MS (m/z): 603.5[M+1]⁺.

Step 9: Synthesis of Compound 2

A solution of 9-((3aR,4R,6R,6aR)-6-((((1r,3S)-3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine (105 mg) in HCl/MeOH (2.5 mol/L) (10 mL) was stirred at RT for 2 h, then concentrated to dryness. K₂CO₃ (96 mg) in water (0.5 mL) and MeOH (5 mL) were added and the resulting mixture was stirred for another 10 min at RT and then filtered. The filtrate was concentrated and the residue was purified by preparative-HPLC (xbridge 30 mm*150 mm, Mobile phase: A: water (10 mM NH4HCO3) B: CAN, Gradient: 35-45% B in 10 min, 45-45% B in 6 min, stop at 20 min, Flow rate: 50 ml/min) to give Compound 2 (50 mg, yield: 51%) as a white solid. $^1$HNMR (500 MHz, MeOD): $\delta_H$ 8.29 (s, 1H), 8.20 (s, 1H), 7.47-7.39 (m, 3H), 5.96 (d, J=4.0 Hz, 1H), 4.70-4.75 (m, 1H), 4.26-4.27 (m, 1H), 4.05-4.06 (m, 1H), 3.140-3.155 (m, 1H), 3.00-2.76 (m, 5H), 2.18-2.16 (m, 2H), 1.87-1.85 (m, 2H), 1.57-1.55 (m, 2H), 1.36 (s, 9H), 1.01 (d, J=6.5 Hz, 3H), 0.94 (d, J=6.5 Hz, 3H) ppm; ESI-MS (m/z): 563.4 [M+1]⁺.

Example 2

Bioassay Protocol and General Methods

Cell Culture. Human hematological tumor cell lines THP-1, RS4; 11, and MV4-11 were obtained from ATCC, MOLM-13 cells were obtained from DSMZ. All lines were grown in RPMI 1640 containing 10% FBS and maintained using the vendors recommended cell densities and environmental conditions. Media was supplemented with non essential amino acids and L-Glutamine. THP-1 cells were also supplemented with 0.05 mM β-Mercaptoethanol.

Methylation Analysis. Cells were seeded at $5\times10^5$ cells/mL in a 12 well plate at a final volume of 2 mLs. Cells were dosed with compounds to the appropriate concentration from a 50 mM DMSO stock solution. Compound and media were refreshed every two days over the course of seven day incubation by counting cells using trypan blue exclusion (Vicell), pelleting at 200 g for 5 minutes and resuspending in fresh media containing compound at a final cell concentration of $5\times10^5$ cells/mL. Following compound incubation, histones were extracted from $1\times10^6$ cells using a commercial histone extraction kit (Active Motif). Purified histones were quantitated using the BCA protein assay (Pierce) with a BSA standard curve. 400 ng of isolated histones were fractionated by SDS-PAGE on a 4-20% gel and transferred to nitrocellulose membranes. Membranes were incubated with various primary and secondary antibodies and imaged on the Licor imaging system (Odyssey). The H3K79-Me2 rabbit polyclonal was purchased from Abcam. Other rabbit polyclonal antibodies including H3K4-Me3, H3K9-Me3, H3K27-Me2, and H3K27-Me3 were purchased from Cell Signaling Technologies (CST). A mouse monoclonal total H3 antibody was used as a loading control (CST). Fluorescently labeled secondary antibodies were purchased from Odyssey.

Cell Growth and Viability Analysis. Cells were harvested from exponentially growing cell cultures and seeded at $3\times10^4$ cells per well. Samples were maintained in a 96 well black walled clear bottom plate (Corning). A final concentration of 50 uM compound in 0.2% DMSO was added to the appropriate wells on Day 0. Treatment of MV4-11 and MOLM-13 lasted 14 days, while THP-1 cells were treated for 18 days. Compound and media were replaced every two days during incubation by transferring samples to a V-bottom plate (Corning), spinning at 200 g for 5 minutes in a room temperature rotor, resuspending in fresh media containing compound and transferring back to the assay plate. Cells were counted periodically using the Guava Viacount assay and read on the EasyCyte Plus instrument (Millipore). Assay plates were split when necessary to within recommended cell densities. Final cell counts were adjusted to take cell splits into account and reported as total viable cells/well.

HOXA9 (qPCR). Cells were treated with compound for 7 days similar to methylation assay. Cell were pelleted at 200 g in a room temperature rotor and total RNA isolated using the Qiagen RNeasy kit. RNA concentration and quality was determined by using the Nanovue (GE Healthcare). Total RNA was reverse transcribed using a high capacity cDNA reverse transcription kit (Applied Biosystems). A predesigned labeled primer set for HOXA9 was purchased from Applied Biosystems. qPCR reactions contained 50 ng cDNA, 1× labeled primer and 1× Taqman universal PCR master mix (Applied Biosystems). Samples were run on a 7900 HT Fast Real Time PCR machine (Applied Biosystems) with PCR conditions of 2 min 50° C., 10 min 95° C., 40 cycles at 15 sec 95° C. and 1 min 60° C. HOXA9 cycle numbers were normalized to the house keeping gene B2 microglobulin (B2M predesigned control from Applied Biosystems). Percent of DMSO control was calculated with the equation, percent control=$(2^{-\Delta\Delta CT})*100$ where the $\Delta\Delta CT$ is the difference between normalized HOXA9 sample and control ($\Delta$CT sample$-\Delta$CT control$=\Delta\Delta$CT). Determination of $IC_{50}$. Test compounds were serially diluted 3 fold in DMSO for 10 points and 1 µl was plated in a 384 well microtiter plate. Positive control (100% inhibition standard) was 2.5 uM final concentration of S-adenosyl-L-homocysteine and negative control (0% inhibition standard) contained 1 µl of DMSO. Compound was then incubated for 30 minutes with 40 µl per well of DOT1L(1-416) (0.25 nM final concentration in assay buffer: 20 mM TRIS, pH 8.0, 10 mM NaCl, 0.002% Tween20, 0.005% Bovine Skin Gelatin, 100 mM KCl, and 0.5 mM DTT). 10 µl per well of substrate mix (same assay buffer with 200 nM S-[methyl-$^3$H]-adenosyl-L methionine, 600 nM of unlabeled S-[methyl-$^3$H]-adenosyl-L methionine, and 20 nM oligonucleosome) was added to initiate the reaction. Reaction was incubated for 120 minutes at room temperature and quenched with 10 µl per well of 100 µM S-methyl-adenosyl-L methionine. For detection, substrate from 50 µl of reaction was immobilized on a 384 well Streptavidin coated Flashplate (Perkin Elmer) (also coated with 0.2% polyethyleneimine) and read on a Top Count scintillation counter (Perkin Elmer).

Example 3

Tumor Anti-Proliferation Assays

In Vitro Anti-Proliferative Assay. The potency and selectivity of the anti-proliferative activity of the compounds of the present invention were assessed using a panel of MLL-rearranged and non-MLL-rearranged human leukemia cell lines. The cell lines used in the study are listed in FIG. 1A. The MLL-rearranged panel included cell lines derived from ALL, AML and biphenotypic leukemias harboring MLL-AF4, MLL-AF9 or MLL-ENL fusions. These cell lines recruit DOT1L. The panel also included five cell lines that do not possess an MLL-rearrangement, and one cell line that bears a partial tandem duplication of the MLL gene (MLL-PTD).

Exponentially growing cells were plated, in triplicate, in 96-well plates at a density of $3\times10^4$ cells/well in a final volume of 150 µl. Cells were incubated in the presence of increasing concentrations of Compound 2. Anti-proliferative activity was determined by cell viability measurements every 3-4 days for up to 14 days. On days of cell counts, growth media and Compound 2 were replaced and cells split back to a density of $5\times10^4$ cells/well.

The half maximal inhibitory concentration ($IC_{50}$) results in FIG. 1 show that Compound 2 demonstrates potent nanomolar anti-proliferative activity against three of four MLL-rearranged cell lines tested (MV4; 11 (MLL-AF4), MOLM-13 (MLL-AF9), and KOPN-8 (MLL-ENL). EOL-1 cells which express an MLL-PTD were also highly sensitive to Compound 2 ($IC_{50}$=11 nM). RS4; 11 cells and two non MLL-rearranged cells (Reh and Kasumi-1) were 1-3 log orders less sensitive, and two non-MLL-rearranged cells (Jurkat and HL-60) showed no activity. Overall, the results indicate that Compound 2 potently and selectively inhibits the proliferation of MLL-rearranged leukemia cell lines and a subset of non-MLL-rearranged leukemia cell lines.

In Vivo Anti-Proliferative Assay. The in vivo anti-tumor activity of the compounds of the present invention were assessed in a mouse xenograft model of MLL-rearranged leukemia.

Four groups of 20 (Groups 1, 3, 4 and 5), and one group of 8 (Group 2) female nude mice (average weight of 0.023 kg) bearing MV4-11 xenograft tumors of sizes ranging from 80-120 mm$^3$ were implanted subcutaneously with minipumps (Alzet Model 2001). Group 1 received vehicle only from the pump. Group 2 received vehicle only from the pump plus ip injections tid (8 hours apart) of vehicle. Group 3 received 112 mg/kg/day from the pump plus ip injections tid (8 hours apart) of 20 mg/kg of Compound 2 for a total daily dose of 172 mg/kg/day. Group 4 and 5 received 112 and 56 mg/kg/day of Compound 2 from the pumps, respectively. Pumps were designed to last for 7 days and were exchanged twice to give total infusion duration of 21 days exposure.

A single blood sample was taken from all animals in Groups 4 and 5 on days 7, 14, and 21 and assayed for plasma levels of Compound 2. Blood samples were taken from Group 3 on days 7 and 14 at the following time points (3 animals per time point): 5 minutes pre-ip dose, and 15 min, 30 min, 1, 2, and 4 hours post ip dose. On day 21 three hours after the last ip injection, a single blood sample was taken from Group 3. Tumor size was measured every 4 days. After 21 days the study was terminated, and mean TGI calculated.

Figure 2:
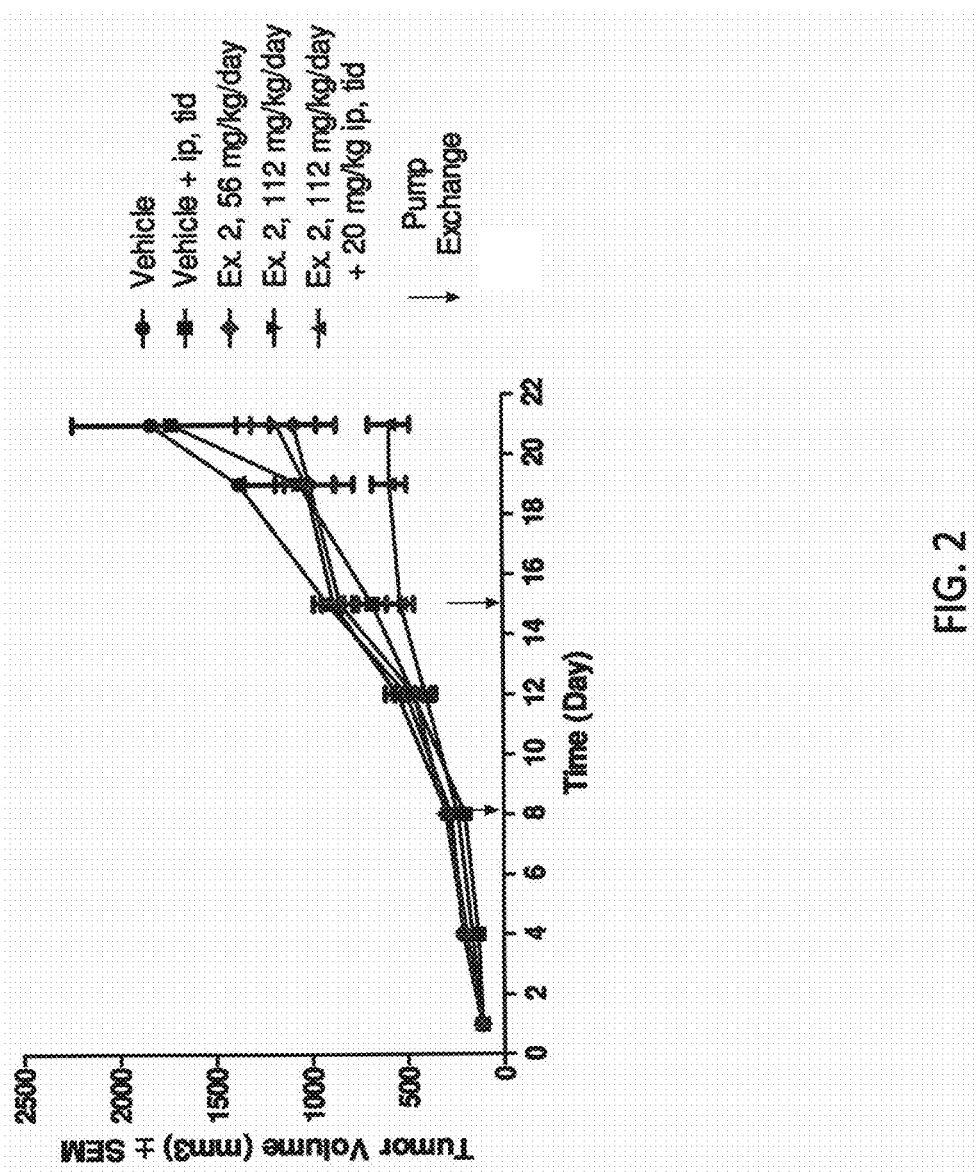
FIG. 2 is a plot showing the tumor growth over 21 days of treatment with control or Compound 2 at various dosages.

FIG. 2 shows the tumor growth over the 21 days of dosing. There was no difference in tumor size between the two vehicle control groups. The high dose minipump group supplemented with ip dosing showed a statistically significant TGI of >70% compared to the controls. The 56 and 112 mg/kg/day groups showed non-statistically significant TGI values of 43 and 38%, respectively, compared to controls. Compound 2 is referred to as Ex. 2 in FIG. 2.

Figure 3A:
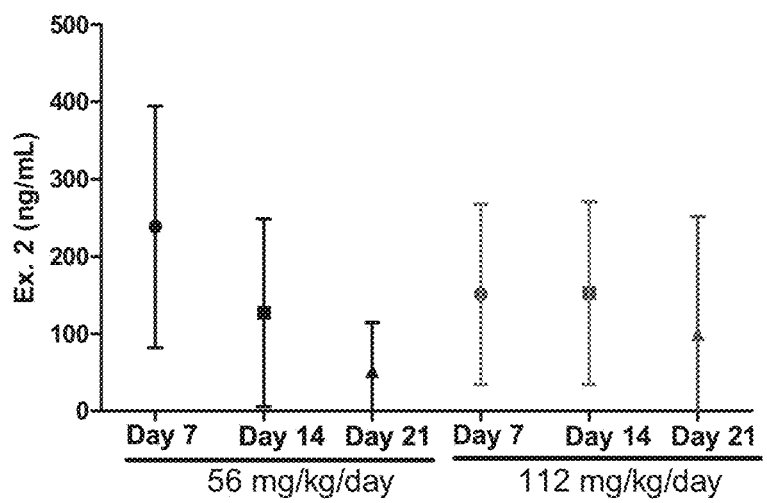
FIG. 3A is a plot showing the estimated steady state plasma concentrations of Compound 2 in Groups 4 and 5 as determined by the averaged blood samples taken on days 7, 14 and 21.

FIG. 3A shows the estimated steady state plasma concentrations of Compound 2 in Groups 4 and 5 as determined by the averaged blood samples taken on days 7, 14, and 21. The data suggest that the average steady state Compound 2 plasma levels ranged from 99 to 152 ng/ml for Group 4, and 52 to 238 ng/ml for Group 5. The average plasma level from the last sampling on day 21 was 99 ng/ml for Group 4 and 52 ng/ml for Group 5.

Figure 3B:
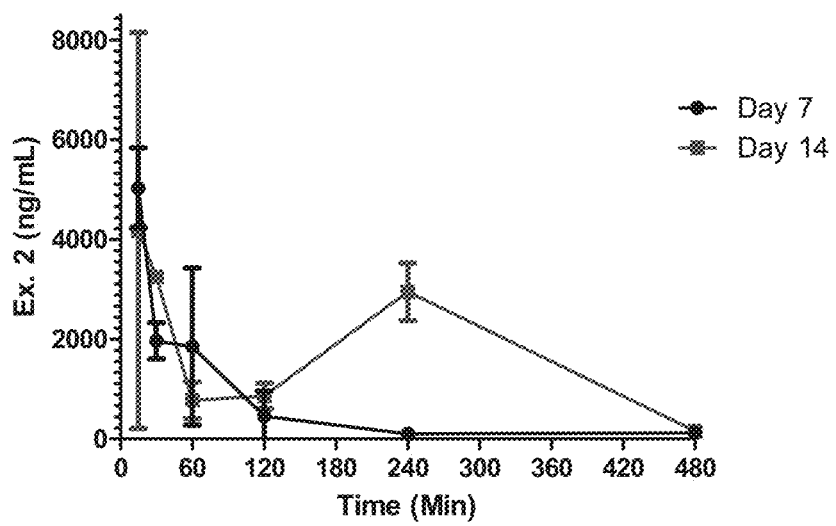
FIG. 3B is a plot showing the Compound 2 plasma concentrations plotted against time after ip injection.

FIG. 3B shows the Compound 2 plasma concentrations plotted against time after ip injection. The ip injections produced a significant increase in plasma exposure to Compound 2 in terms of both the $C_{max}$ (4200 to 5000 ng/ml) after each of the tid injections and the daily AUCs over those produced by the steady state plasma level resulting from the continuous infusion. Overall, the results indicate that Compound 2 demonstrated significant anti-tumor activity in a mouse xenograft model of MLL-rearranged leukemia.

Example 4

A First-In-Human Phase 1 and Expanded Cohort Study of Compound 2 in Advanced Hematologic Malignancies, Including Acute Leukemia with Rearrangement of the MLL Gene A study is carried out to determine the safe dose of Compound 2, to evaluate the safety of Compound 2 in patients with advanced hematologic malignancies, and to conduct a preliminary assessment of the anti-leukemia activity of Compound 2 in patients with acute leukemias bearing rearrangements of the MLL gene. Conditions for this study include Acute Myeloid Leukemia, Acute Lymphoblastic Leukemia, Myelodysplastic Syndrome, A myeloproliferative disorder, and Chronic Myelogenous Leukemia.

Details of the study are shown in the table 1 below.

TABLE 1

Study Design.

| | Measure | Time Frame | Designated as safety issue | Analysis |
|---|---|---|---|---|
| Primary Outcome Measure | The maximum tolerated dose (MTD) of Compound 2 as determined by incidence of protocol-specified dose-limiting adverse events | up to 12 months | yes | The MTD is defined as one dose level below the level in which >1 dose-limiting adverse events (as defined by the protocol) are observed. |
| Secondary Outcome Measures | Pharmacokinetic profile of Compound 2 | up to 12 months | no | Analysis of Cmax, AUC and steady state concentration |
| | The type, incidence, and severity of adverse events in patients treated with Compound 2 | up to 24 months | yes | Evaluation of adverse events, vital signs, physical examination, 12-lead ECG, and laboratory assessments |
| | Anti-leukemic activity of Compound 2 in patients with acute leukemia harboring a MLL-rearrangement | up to 24 months | no | Evaluation of response by standard criteria for AML or ALL |
| | Effects of Compound 2 on histone H3K79 methylation in peripheral blood mononuclear (PBMC) and leukemia cells; and target gene expression in leukemia cells. | up to 24 months | no | / |

A subset of patients with acute myeloid leukemia (AML) and acute lymphoblastic leukemia (ALL) harbor rearrangements of the MLL gene, which are detected either by cytogenetic or fluorescent in-situ hybridization evaluation at the time of diagnosis. DOT1L plays an important role in the malignant process in these leukemias, and Compound 2 is a molecule that blocks the activity of DOT1L.

Compound 2 is administered as a 21-day continuous intravenous infusion, and safe dosages are assessed in patients with hematologic malignancies. The study will have two phases. The first phase will assess escalating doses of Compound 2 in order to determine the maximally tolerated dose (MTD) of Compound 2. Once the MTD is established, a second phase of the study will further evaluate the safety of Compound 2 and assess the anti-leukemia activity of Compound 2 in MLL-rearranged leukemia.

| Arms | Assigned Interventions |
|---|---|
| Experimental: Compound 2 Dose-escalation and extension cohorts | Drug: Compound 2 Dose-escalation, 21-day continuous IV infusion of each 28-day cycle. Number of cycles: until disease progression or unacceptable toxicity develops. |

Eligibility for Patients
1. Ages Eligible for Study: 18 Years and older
2. Genders Eligible for Study: Both
Inclusion Criteria:
1. Male and female patients aged ≥18 years.
2. AML, ALL, acute mixed lineage leukemia, myelodysplastic syndrome (International Prognostic Scoring System Int-2 or high-risk), myeloproliferative disorder, or chronic myelogenous leukemia meeting the following criteria (only patients with acute leukemia with rearrangement of the MLL gene will be eligible for the expanded cohort):
   At least one prior therapy;
   Refractory disease on most recent therapy, or disease recurrence following remission on most recent therapy;
   Received and failed all known effective therapies for their disease; and/or
   Not a candidate for allogeneic stem cell transplantation.
3. Eastern Cooperative Oncology Group (ECOG) performance status of 0-2.
4. Patients must have the following clinical laboratory values:
   Serum creatinine ≤2 mg/dL or creatinine clearance >60 mL/minute;
   Total bilirubin ≤1.5 times the ULN for the institution, unless considered due to Gilbert's syndrome;
   ALT or AST ≤twice the upper limit of normal (ULN), unless considered due to organ leukemic involvement;
   Absolute neutrophil count ≥1,000/µL (unless due to documented leukemic involvement of the bone marrow at the time of study entry);
   Platelets ≥100,000/µL (unless due to documented leukemic involvement of the bone marrow at the time of study entry); and
   PT or aPTT <1.5 times the ULN.
5. Able and willing to give written informed consent.
6. Life expectancy of at least 3 months.
Exclusion Criteria:
1. Uncontrolled intercurrent illness or psychiatric illness/social situations that would limit compliance with study requirements.
2. Active heart disease.
3. Receiving any other standard treatment for their hematologic malignancy.
4. Receiving strong CYP3A4 inhibitors/inducers.
5. Known history of cerebrovascular accident in the past 6 months.
6. Known bleeding diathesis.
7. Known, active involvement of the central nervous system by leukemia.
8. On immunosuppressive therapy.
9. Known active infection.
10. Pregnant or nursing females.

INCORPORATION BY REFERENCE

The entire disclosure of each of the patent documents and scientific articles referred to herein is incorporated by reference for all purposes.
Equivalents
The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for treating a hematological cancer comprising administering to a subject in need thereof a therapeutically effective amount of a compound of Formula (I) or its N-oxide or a pharmaceutically acceptable salt thereof:

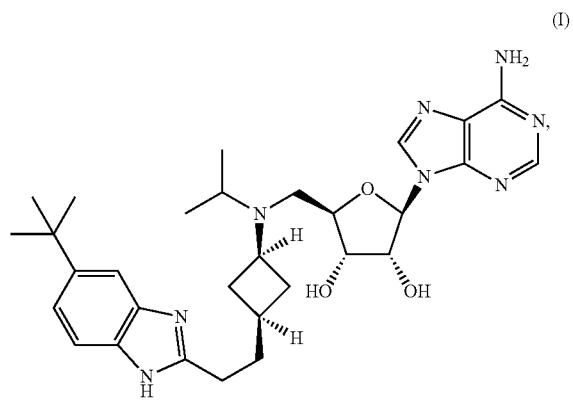 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

wherein the subject had at least one prior therapy to treat a hematological cancer and wherein the hematological cancer is refractory to at least one of the prior therapies.

2. The method of claim 1, wherein the subject received and failed all known effective therapies for the hematological cancer.

3. The method of claim 1, wherein the hematological cancer is selected from the group consisting of acute myeloid leukemia, acute lymphoblastic leukemia, myelodysplastic syndrome, a myeloproliferative disorder, and chronic myelogenous leukemia.

4. The method of claim 1, wherein the hematological cancer is leukemia.

5. The method of claim 4, wherein the subject has a leukemia characterized by MLL gene rearrangement.

6. The method of claim 5, wherein the MLL gene rearrangement is translocation of the MLL gene at 11q23.

7. The method of claim 5, wherein the MLL gene rearrangement is a partial tandem duplication of the MLL gene.

8. The method of claim 1, wherein the subject is simultaneously being treated with another therapy to treat acute myeloid leukemia, acute lymphoblastic leukemia, myelodysplastic syndrome, a myeloproliferative disorder, or chronic myelogenous leukemia.

9. The method of claim 8, wherein the another therapy is standard of care for the treatment of acute myeloid leukemia.

10. The method of claim 8, wherein the another therapy is standard of care for the treatment of acute lymphoblastic leukemia.

11. A method for treating a hematological cancer comprising administering to a subject in need thereof a therapeutically effective amount of a compound of Formula (I) or its N-oxide or a pharmaceutically acceptable salt thereof:

(I)

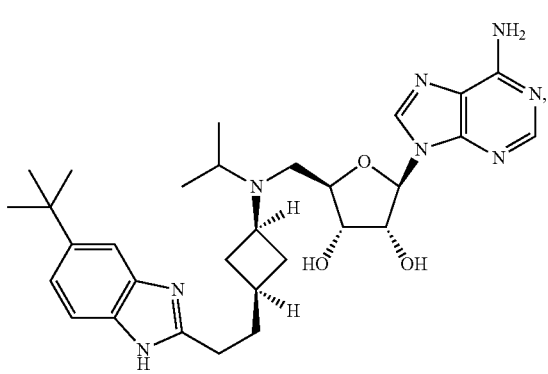

wherein the subject had at least one prior therapy to treat a hematological cancer and wherein the hematological cancer shows recurrence following remission.

12. The method of claim 11, wherein the subject received and failed all known effective therapies for the hematological cancer.

13. The method of claim 11, wherein the hematological cancer is selected from the group consisting of acute myeloid leukemia, acute lymphoblastic leukemia, myelodysplastic syndrome, a myeloproliferative disorder, and chronic myelogenous leukemia.

14. The method of claim 11, wherein the hematological cancer is leukemia.

15. The method of claim 14, wherein the subject has a leukemia characterized by MLL gene rearrangement.

16. The method of claim 15, wherein the MLL gene rearrangement is translocation of the MLL gene at 11q23 or a partial tandem duplication of the MLL gene.

17. The method of claim 11, wherein the subject is simultaneously being treated with another therapy to treat acute myeloid leukemia, acute lymphoblastic leukemia, myelodysplastic syndrome, a myeloproliferative disorder, or chronic myelogenous leukemia.

18. The method of claim 17, wherein the another therapy is standard of care for the treatment of acute myeloid leukemia.

19. The method of claim 17, wherein the another therapy is standard of care for the treatment of acute lymphoblastic leukemia.

20. A method for treating a hematological cancer comprising administering to a subject in need thereof a therapeutically effective amount of a compound of Formula (I) or its N-oxide or a pharmaceutically acceptable salt thereof:

(I)

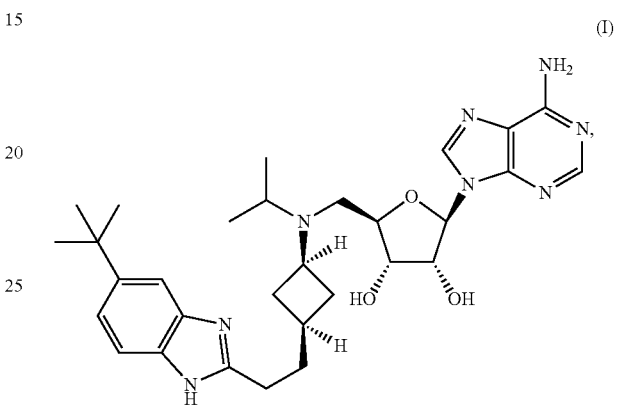

wherein the subject is unable to receive other therapy to treat the cancer due to age or intercurrent illness and wherein the hematological cancer is refractory to a prior therapy or the hematological cancer shows recurrence following remission.

* * * * *